(12) United States Patent
Candau

(10) Patent No.: US 6,699,461 B2
(45) Date of Patent: Mar. 2, 2004

(54) UV-PHOTOSTABILIZED SUNSCREEN COMPOSITIONS COMPRISING DIBENZOYLMETHANE/BENZOPHENONE COMPOUNDS

(75) Inventor: Didier Candau, Bievres (FR)

(73) Assignee: Societe L'Oreal S.A., Paris (FR)

( * ) Notice: Subject to any disclaimer, the term of this patent is extended or adjusted under 35 U.S.C. 154(b) by 0 days.

(21) Appl. No.: 10/314,186

(22) Filed: Dec. 9, 2002

(65) Prior Publication Data
US 2003/0161793 A1 Aug. 28, 2003

(30) Foreign Application Priority Data
Dec. 7, 2001 (FR) .............................. 01 15858

(51) Int. Cl.$^7$ .............................. A61K 7/42; A61K 7/44; A61K 7/00
(52) U.S. Cl. .......................... 424/59; 424/60; 424/400; 424/401
(58) Field of Search .......................... 424/59, 60, 400, 424/401

(56) References Cited

U.S. PATENT DOCUMENTS 6,387,355 B2 * 5/2002 Heidenfelder et al. ........ 424/59

FOREIGN PATENT DOCUMENTS

EP 1 046 391 A2 10/2000
EP 1 133 980 A2 9/2001

OTHER PUBLICATIONS

French Search Report Issued for FR 01/15858 on Sep. 27, 2002—2 pages.

* cited by examiner

*Primary Examiner*—Shelley A. Dodson
(74) *Attorney, Agent, or Firm*—Burns, Doane, Swecker & Mathis, L.L.P.

(57) ABSTRACT

Topically applicable cosmetic/dermatological sunscreen compositions well suited for the stable UV-photoprotection of human skin and/or hair are devoid of any p-methylbenzylidenecamphor, but contain (a) an effective photoprotecting amount of at least one UV-screening dibenzoylmethane compound, and (b) an effective photostabilizing amount of at least on UV-screening amino-substituted 2-hydroxybenzophenone compound having the following structural formula (I):

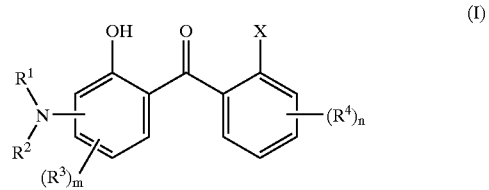

formulated into (c) a topically applicable, cosmetically/dermatologically acceptable vehicle, diluent or carrier therefor.

27 Claims, No Drawings

UV-PHOTOSTABILIZED SUNSCREEN COMPOSITIONS COMPRISING DIBENZOYLMETHANE/BENZOPHENONE COMPOUNDS

CROSS-REFERENCE TO PRIORITY APPLICATION

This application claims priority under 35 U.S.C. §119 of FR-01/15858, filed Dec. 7, 2001, hereby expressly incorporated by reference.

BACKGROUND OF THE INVENTION

1. Technical Field of the Invention

The invention relates to a cosmetic or dermatological composition for topical use, characterized in that it comprises, in a cosmetically acceptable vehicle:
  (a) at least one UV screening agent of the dibenzoylmethane derivative type and
  (b) at least one specific amino-substituted 2-hydroxybenzophenone derivative; the said composition not comprising p-methylbenzylidenecamphor.

The invention also relates to a process for improving the stability with respect to UV radiation of at least one dibenzoylmethane derivative present in a cosmetic or dermatological composition not comprising p-methylbenzylidenecamphor which consists in combining, with the said dibenzoylmethane derivatives, an effective amount of at least one specific amino-substituted 2-hydroxybenzophenone derivative.

2. Description of the Prior Art

It is known that light radiation with wavelengths of between 280 nm and 400 nm makes possible browning of the human epidermis and that rays with wavelengths more particularly of between 280 and 320 nm, known under the name of UV-B, cause erythemas and skin burns which may be harmful to the development of natural tanning. For these reasons and for aesthetic reasons, there exists a continual demand for means for controlling this natural tanning, for the purpose of thus controlling the color of the skin; it is thus advisable to screen out this UV-B radiation.

It is also known that UV-A rays, with wavelengths of between 320 and 400 nm, which cause browning of the skin, are capable of bringing about a detrimental change in the latter, in particular in the case of sensitive skin or of skin continually exposed to solar radiation. UV-A rays cause in particular a loss in the elasticity of the skin and the appearance of wrinkles, resulting in premature aging of the skin. They promote the triggering of the erythemal reaction or accentuate this reaction in some subjects and can even be the cause of phototoxic or photoallergic reactions. Thus, for aesthetic and cosmetic reason, such preservation of the natural elasticitiy of the skin, for example, more and more people with to control the effect of UV-A radiation on their skin. It is therefore desirable also to screen out UV-radiation.

In this respect, a particular advantageous family of UV-A screening agents is currently composed of dibenzoylmethane derivatives and in particular 4-tert-butyl-4'-methoxydibenzoylmethane; this is because derivatives exhibit a high intrinsic absorbance. These dibenzoylmethane derivatives, which are now products well known per se as screening agents active in the UV-A region, are disclosed in particular in French Patent Applications FR-A-2 326 405 and FR-A-2 440 933 and in European Patent Application EP-A-0 114 607; furthermore, 4-tert-butyl-4'-methoxydibenzoylmethane is currently offered for sale under the trademark of "Parsol 1789" by Hoffmann-LaRoche.

Unfortunately, it is found that dibenzoylmethane derivatives are products which are relatively sensitive to ultraviolet radiation (in particular UV-A radiation), that is to say, more specifically, that they have an unfortunate tendency to decompose more or less rapidly under the effect of the latter. Thus, this substantial lack of photochemical stability of dibenzoylmethane derivatives in the face of ultraviolet radiation, to which they are naturally intended to be subjected, does not make it possible to guarantee constant protection during prolonged exposure to the sun, so that repeated applications at regular and frequent intervals have to be carried out by the user in order to obtain effective protection of the skin against UV radiation.

The photostabilization of dibenzoylmethane derivatives with respect to UV radiation constitutes, to date, a problem which has not yet been solved in a completely satisfactory manner.

Antisun compositions formed from amino-substituted 2-hydroxybenzophenone derivatives which can comprise other additional screening agents, such as dibenzoylmethane derivatives, in the presence of p-methylbenzylidenecamphor, are known in Patent Applications DE 10 012 408 and EP-A-1 046 391.

SUMMARY OF THE INVENTION

In point of fact, the Applicant company has now just discovered, surprisingly, that, by combining the abovementioned dibenzoylmethane derivatives with an amount of at least one specific amino-substituted 2-hydroxybenzophenone derivative, it is possible to improve, substantially and notably, the photochemical stability (or photostability) of these same dibenzoylmethane derivatives.

Thus, in accordance with one of the subject-matters of the present invention, a novel cosmetic or dermatological composition for topical use is now provided, which composition is characterized in that it comprises, in a cosmetically acceptable vehicle:
  (a) at least one UV screening agent of the dibenzoylmethane derivative type and
  (b) at least one specific amino-substituted 2-hydroxybenzophenone derivative of formula (I) which will be defined later; the said composition not comprising p-methylbenzylidenecamphor.

The invention also relates to a process for improving the stability with respect to UV radiation of at least one dibenzoylmethane derivative in a cosmetic or dermatological composition not comprising p-methylbenzylidenecamphor which consists in combining, with the said dibenzoylmethane derivative, an effective amount of at least one specific amino-substituted 2-hydroxybenzophenone derivative.

The term "effective amount of amino-substituted 2-hydroxybenzophenone derivative" in accordance with the invention is understood to mean an amount sufficient to produce a noteworthy and significant improvement in the photostability of the dibenzoylmethane derivative or derivatives of the photoprotective cosmetic composition. This minimum amount of photostabilizing agent to be employed, which can vary depending on the nature of the cosmetically acceptable vehicle used for the composition, can be determined without any difficulty by means of a conventional test for measuring photostability.

Finally, another subject-matter of the present invention is the use of an amino-substituted 2-hydroxybenzophenone derivative of formula (I) in the preparation of a cosmetic or dermatological composition comprising at least one dibenzoylmethane derivative and not comprising p-methylbenzylidenecamphor for the purposed of improving the stability with respect to UV radiation of the said dibenzoylmethane derivative present.

Other characteristics, aspects and advantages of the present invention will become apparent on reading the detailed description which will follow.

DETAILED DESCRIPTION OF BEST MODE AND SPECIFIC/PREFERRED EMBODIMENTS OF THE INVENTION

The ratio by weight of the amino-substituted 2-hydroxybenzophenone derivative to the dibenzoylmethane derivative is preferably greater than 1.

The amino-substituted 2-hydroxybenzophenone derivatives in accordance with the invention correspond to the following formula (I):

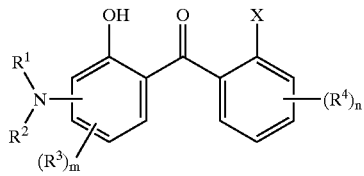

in which:

$R^1$ and $R^2$, which may be identical or different, denote a hydrogen atom, a $C_1$–$C_{20}$ alkyl radical, a $C_2$–$C_{10}$ alkenyl radical, a $C_3$–$C_{10}$ cycloalkyl radical or a $C_3$–$C_{10}$ cycloalkenyl radical;

$R^1$ and $R^2$ can also form, with the nitrogen atom with which they are bonded, a 5- or 6-membered heterocyclic ring member;

$R^3$ and $R^4$, which may be identical or different, denote a $C_1$–$C_{20}$ alkyl radical, a $C_2$–$C_{10}$ alkenyl radical, a $C_3$–$C_{10}$ cycloalkyl radical, a $C_3$–$C_{10}$ cycloalkenyl radical, a $C_1$–$C_{12}$ alkoxy radical, a ($C_1$–$C_{20}$)alkoxycarbonyl radical, a $C_1$–$C_{12}$ alkylamino radical, a di($C_1$,$C_{12}$)alkylamino radical, an aryl radical or a heteroaryl which is optionally substituted, or a water-solubilizing substituent chosen from a carboxylate group, a sulphonate group or an ammonium residue;

X denotes a hydrogen atom or a $COOR^5$ or $CONR^6R^7$ group;

$R^5$, $R^6$ and $R^7$, which may be identical or different, denote a hydrogen atom, a $C_1$–$C_{20}$ alkyl radical, a $C_2$–$C_{10}$ alkenyl radical, a $C_3$–$C_{10}$ cycloalkyl radical, a $C_3$–$C_{10}$ cycloalkenyl radical, a —(YO))$_0$—Z group or an aryl group;

Y denotes —$(CH_2)_2$—, —$(CH_2)_3$—, —$(CH_2)_4$—or —CH—$(CH_3)$—$CH_2$—;

Z represents —$CH_2$—$CH_3$, —$CH_2CH_2CH_3$, —$CH_2$—$CH_2$—$CH_2$—$CH_3$ or —CH $(CH_3)$—$CH_3$;

m is an integer varying from 0 to 3;

n is an integer varying from 0 to 3;

o is an integer varying from 1 to 2.

Mention may be made, as $C_1$–$C_{20}$ alkyl radicals, of, for example: methyl, ethyl, n-propyl, 1-methylethyl, n-butyl, 1-methylpropyl, 2-methylpropyl, 1,1-dimethyl-ethyl, n-pentyl, 1-methylbutyl, 2-methylbutyl, 3-methyl-butyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,2,2-trimethylpropyl, 1-ethyl-1-methylpropyl, 1-ethyl-2-methylpropyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl or n-icosyl.

Mention may be made, as $C_2$–$C_{10}$ alkenyl groups, of, for example: vinyl, n-propenyl, isopropenyl, 1-butenyl, 2-butenyl, 1-pentenyl, 2-pentenyl, 2-methyl-1-butenyl, 2-methyl-2-butenyl, 3-methyl-1-butenyl, 1-hexenyl, 2-hexenyl, 1-heptenyl, 2-heptenyl, 1-octenyl or 2-octenyl.

Mention may be made, as $C_1$–$C_{12}$ alkoxy radicals, of: methoxy, ethoxy, n-propoxy, n-butoxy, n-pentoxy, 1-methylpropoxy, 3-methylbutoxy, 2,2-dimethylpropoxy, 1-methyl-1-ethylpropoxy, octoxy, 2-methylpropoxy, 1,1-dimethylpropoxy, hexoxy, heptoxy or 2-ethylhexoxy.

Mention may be made, as $C_3$–$C_{10}$ cycloalkyl radicals, of, for example: cyclopropyl, cyclobutyl, cyclopentyl, cyclohexyl, cycloheptyl, 1-methylcyclo-propyl, 1-ethylcyclopropyl, 1-propylcyclopropyl, 1-butylcyclopropyl, 1-pentylcyclopropyl, 1-methyl-1-butylcyclopropyl, 1,2-dimethylcyclopropyl, 1-methyl-2-ethylcyclopropyl, cyclooctyl, cyclononyl or cyclodecyl.

Mention may be made, as $C_3$–$C_{10}$ cycloalkenyl radicals having one or more double bonds, of: cyclopropenyl, cyclobutenyl, cyclopentenyl, cyclopentadienyl, cyclohexenyl, 1,3-cyclohexadienyl, 1,4-cyclohexadienyl, cycloheptenyl, cycloheptatrienyl, cyclooctenyl, 1,5-cyclooctadienyl, cyclooctatetraenyl, cyclononenyl or cyclodecenyl.

The cycloalkyl or cycloalkenyl radicals can comprise one or more substituents (preferably from 1 to 3) chosen, for example, from halogen, such as chlorine, fluorine or bromine; cyano; nitro; amino; $C_1$–$C_4$ alkylamino; di($C_1$–$C_4$) alkylamino; $C_1$–$C_4$ alkyl; $C_1$–$C_4$ alkoxy; or hydroxyl. They can also comprise from 1 to 3 heteroatoms, such as sulphur, oxygen or nitrogen, the free valencies of which can be occupied by a hydrogen or a $C_1$–$C_4$ alkyl radical.

The aryl groups are preferably chosen from phenyl or naphthyl rings which can comprise one or more substituents (preferably from 1 to 3) chosen, for example, from halogen, such as chlorine, fluorine or bromine; cyano; nitro; amino; $C_1$–$C_4$ alkylamino; di($C_1$–$C_4$)alkylamino; $C_1$–$C_4$ alkyl; $C_1$–$C_4$ alkoxy; or hydroxyl. Preference is more particularly given to phenyl, methoxyphenyl and naphthyl.

The heteroaryl groups generally comprise one or more heteroatoms chosen from sulphur, oxygen or nitrogen.

The water-solubilizing groups are, for example, carboxylate or sulphonate groups and more particularly their salts with physiologically acceptable cations, such as alkali metal salts or trialkylammonium salts, such as tri(hydroxyalkyl)-ammonium or 2-methylpropan-1-ol-2-ammonium salts. Mention may also be made of ammonium groups, such as alkylammoniums, and their salified forms with physiologically acceptable anions.

Mention may in particular be made, as examples of the 5- or 6-membered heterocyclic ring member; formed by the $R^1$ and $R^2$ radicals with the nitrogen atom, of pyrrolidine or piperidine.

The amino groups can be attached to the benzene ring in the ortho, meta or para position with respect to the carbonyl radical and more preferably in the para position.

A family of preferred compounds of formula (I) comprises those chosen from those of following formula (Ia):

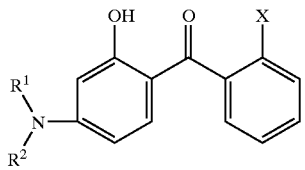

in which:

$R^1$ and $R^2$, which may be identical or different, denote a hydrogen atom or a $C_1$–$C_{12}$ alkyl radical or form, with the nitrogen atom with which they are bonded, a 5- or 6-membered heterocyclic ring member;

X denotes $COOR^5$ or $CONR^6R^7$;

$R^5$ denotes a hydrogen atom, a $C_1$–$C_{12}$ alkyl radical or a $C_3$–$C_6$ cycloalkyl radical;

$R^6$ and $R^7$, which may be identical or different, denote a hydrogen atom, a $C_1$–$C_{12}$ alkyl radical or a $C_5$–$C_6$ cycloalkyl radical.

The more particularly preferred compounds of formula (Ia) are those for which:

$R^1$ and $R^2$, which may be identical or different, denote a $C_1$–$C_4$ alkyl radical and more particularly ethyl;

$R^5$ denotes a $C_3$–$C_8$ alkyl radical;

$R^6$ and $R^7$, which may be identical or different, denote a $C_1$–$C_8$ alkyl radical.

Another family of preferred compounds of formula (I) comprises those chosen from those of following formula (Ib):

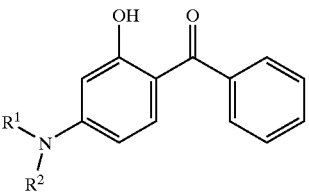

in which:

$R^1$ and $R^2$, which may be identical or different, denote a $C_1$–$C_2$ alkyl radical or form, with the nitrogen atom with which they are bonded, a 5- or 6-membered heterocyclic ring member;.

Mention may more particularly be made, among the compounds of formula (Ib), of:

4-diethylamino-2-hydroxyphenyl phenyl ketone, 4-pyrrolidino-2-hydroxyphenyl phenyl ketone.

A family of more particularly preferred compounds of formula (I) comprises those chosen from those of following formula (Ic):

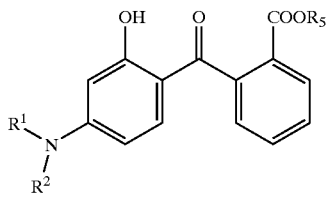

in which:

$R^1$ and $R^2$, which may be identical or different, denote a hydrogen atom or a $C_1$–$C_8$ alkyl radical or form, with the nitrogen atom with which they are bonded, a 5- or 6-membered heterocyclic ring member;

$R^5$ denotes a hydrogen atom, a $C_1$–$C_{12}$ alkyl radical or a $C_3$–$C_6$ cycloalkyl radical.

Mention may be made, among the compounds of formula (Ic), of:

2-(4-pyrrolidino-2-hydroxybenzoyl)benzoate methyl 2-(4-diethylamino-2-hydroxybenzoyl)benzoate 2-ethylhexyl 2-(4-diethylamino-2-hydroxybenzoyl)-benzoate cyclohexyl 2-(4-diethylamino-2-hydroxybenzoyl)-benzoate n-hexyl 2-(4-diethylamino-2-hydroxybenzoyl)benzoate

[lacuna] 2-(4-dibutylamino-2-hydroxybenzoyl)benzoate methyl 2-(4-dibutylamino-2-hydroxybenzoyl)benzoate isobutyl 2-(4-dibutylamino-2-hydroxybenzoyl)benzoate.

A very particularly preferred compound of formula (I) is n-hexyl 2-(4-diethylamino-2-hydroxy-benzoyl) benzoate.

The compounds of formula (I) as defined above are known per se and their structures and their syntheses are disclosed in Patent Applications EP-A-1 046 391 and DE 100 12 408 (which form an integral part of the content of the description).

The amino-substituted 2-hydroxybenzophenone derivatives in accordance with the invention are preferably present in the composition of the invention in proportions preferably ranging from 0.1 to 15% by weight and more preferably from 1 to 10% by weight and more particularly from 2 to 8% by weight with respect to the total weight of the composition.

As indicated above, the dibenzoylmethane derivatives intended to be photostabilized in the context of the present invention are products which are already well known per se and which are disclosed in particular in the abovementioned documents FR 2 326 405, FR 2 440 933 and EP 0 114 607, the teachings of which documents are, insofar as they affect the actual definition of these products, entirely included by way of references in the present description.

According to the present invention, it is possible, of course, to employ one or more dibenzoylmethane derivatives.

Mention may in particular be made, among dibenzoylmethane derivatives coming particularly well within the scope of the present invention, of, without limitation:

2-methyldibenzoylmethane, 4-methyldibenzoylmethane, 4-isopropyldibenzoylmethane, 4-tert-butyldibenzoylmethane, 2,4-dimethyldibenzoylmethane, 2,5-dimethyldibenzoylmethane,
4,4'-diisopropyldibenzoylmethane,
4,4'-dimethoxydibenzoylmethane,
4-tert-butyl-4'-methoxydibenzoylmethane,
2-methyl-5-isopropyl-4'-methoxydibenzoyl methane,
2-methyl-5-tert-butyl-4'-methoxydibenzoylmethane,
2,4-dimethyl-4'-methoxydibenzoylmethane,
2,6-dimethyl-4-tert-butyl-4'-methoxydibenzoylmethane.

Preference is very particularly given according to the present invention, among the abovementioned dibenzoylmethane derivatives, to the use of 4-tert-butyl-4'-methoxydibenzoylmethane, in particular that offered for sale under the trademark of "Parsol 1789" by Hoffmann-LaRoche, this screening agent corresponding to the following expanded formula:

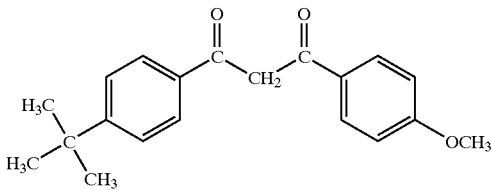

Another preferred dibenzoylmethane derivative according to the present invention is 4-isopropyldibenzoylmethane, a screening agent sold under the name of "Eusolex 8020" by Merck and corresponding to the following expanded formula (II):

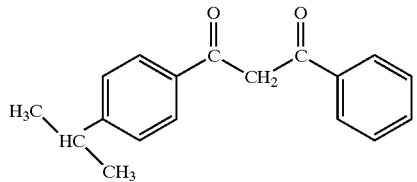

The dibenzoylmethane derivative or derivatives are present in the compositions in accordance with the invention at contents preferably ranging from 0.5 to 15% by weight and more preferably from 1% to 10% by weight and more particularly from 2 to 8% by weight, with respect to the total weight of the composition.

In addition, the compositions in accordance with the invention can comprise other additional, organic UV screening agents which are active in the UV-A and/or UV-B regions (absorbers), the said screening agents being water-soluble, fat-soluble or insoluble in commonly used cosmetic solvents.

The additional organic UV screening agents are chosen in particular from anthranilates; salicylic derivatives; cinnamic derivatives; camphor derivatives, other than the p-methylbenzylidenecamphor; triazine derivatives, such as those disclosed in U.S. Pat. No. 4,367,390, EP 863 145, EP 517 104, EP 570 838, EP 796 851, EP 775 698, EP 878 469 and EP 933 376; benzophenone derivatives, other than those of formula (I); β,β-diphenylacrylate derivatives; benzotriazole derivatives; benzalmalonate derivatives; benzimidazole derivatives; imidazolines; p-aminobenzoic acid (PABA) derivatives; methylenebis(hydroxyphenylbenzotriazole) derivatives as disclosed in Applications U.S. Pat. No. 5,237,071, U.S. Pat. No. 5,166,355, GB 2 303 549, DE 197 26 184 and EP 893 119; screening polymers and screening silicones, such as those disclosed in particular in Application WO 93/04665; dimers derived from α-alkylstyrene, such as those disclosed in Patent Application DE 198 55 649; and 4,4-diarylbutadienes as disclosed in Applications EP 0 967 200, DE 197 46 654, DE 197 55 649 and EP-A-1 008 586.

Mention may be made, as examples of additional organic screening agents, of, denoted below under their INCI names:

para-Aminobenzoic Acid Derivatives:
  PABA,
  Ethyl PABA,
  Ethyl Dihydroxypropyl PABA,
  Ethylhexyl Dimethyl PABA, sold in particular under the name "Escalol 507" by ISP,
  Glyceryl PABA,
  PEG-25 PABA, sold under the name "Uvinul P25" by BASF,
Salicylic Derivatives:
  Homosalate, sold under the name "Eusolex HMS" by Rona/EM Industries,
  Ethylhexyl Salicylate, sold under the name "Neo Heliopan TS" by Haarmann and Reimer,
  Dipropyleneglycol Salicylate, sold under the name "Dipsal" by Scher,
  TEA Salicylate, sold under the name "Neo Heliopan TS" by Haarmann and Reimer,
Cinnamic Derivatives:
  Ethylhexyl Methoxycinnamate, sold in particular under the trademark "Parsol MCX" by Hoffmann-LaRoche,
  Isopropyl Methoxy cinnamate,
  Isoamyl Methoxy cinnamate, sold under the trademark "Neo Heliopan E 1000" by Haarmann and Reimer,
  Cinoxate,
  DEA Methoxycinnamate,
  Diisopropyl Methylcinnamate,
  Glyceryl Ethylhexanoate Dimethoxycinnamate,
β,β-Diphenylacrylate Derivatives:
  Octocrylene, sold in particular under the trademark "Uvinul N539" by BASF,
  Etocrylene, sold in particular under the trademark "Uvinul N35" by BASF,
Benzophenone Derivatives:
  Benzophenone-1, sold under the trademark "Uvinul 400" by BASF,
  Benzophenone-2, sold under the trademark "Uvinul D50" by BASF,
  Benzophenone-3 or Oxybenzone, sold under the trademark "Uvinul M40" by BASF,
  Benzophenone-4, sold under the trademark "Uvinul MS40" by BASF,
  Benzophenone-5,
  Benzophenone-6, sold under the trademark "Helisorb 11" by Norquay,
  Benzophenone-8, sold under the trademark "Spectra-Sorb UV-24" by American Cyanamid,
  Benzophenone-9, sold under the trademark "Uvinul DS-49" by BASF,
  Benzophenone-12,
Benzylidenecamphor Derivatives:
  3-Benzylidene camphor, manufactured under the name "Mexoryl SD" by Chimex,
  Benzylidene Camphor Sulfonic Acid, manufactured under the name "Mexoryl SL" by Chimex, Camphor Benzalkonium Methosulfate, manufactured under the name "Mexoryl SO" by Chimex, Terephthalyidene Dicamphor Sulfonic Acid, manufactured under the name "Mexoryl SX" by Chimex, Polyacrylamidomethyl Benzylidene Camphor, manufactured under the name "Mexoryl SW" by Chimex, Phenylbenzimidazole Derivatives:

Phenylbenzimidazole Sulfonic Acid, sold in particular under the trademark "Eusolex 232" by Merck, Disodium Phenyl Dibenzimidazole Tetrasulfonate, sold under the trademark "Neo Heliopan AP" by Haarmann and Reimer, Triazine Derivatives:

Anisotriazine, sold under the trademark "Tinosorb S" by Ciba Specialty Chemicals, Ethylhexyl triazone, sold in particular under the trademark "Uvinul T150" by BASF, Diethylhexyl Butamido Triazone, sold under the trademark "Uvasorb HEB" by Sigma 3V, 2,4,6-tris(diisobutyl 4'-aminobenzalmalonate)-s-triazine, Phenylbenzotriazole Derivatives:

Drometrizole Trisiloxane, sold under the name "Silatrizole" by Rhodia Chimie,

Methylenebis(benzotriazolyltetramethylbutyl-phenol), sold in the solid form under the trademark "Mixxim BB/100" by Fairmount Chemical or in the micronized form in aqueous dispersion under the trademark "Tinosorb M" by Ciba Specialty Chemicals, Anthranilic Derivatives:

Menthyl anthranilate, sold under the trademark "Neo Heliopan MA" by Haarmann and Reimer, Imidazoline Derivatives:

Ethylhexyl Dimethoxybenzylidene Dioxoimidazoline Propionate,

Benzalmalonate Derivatives:

Polyorganosiloxane comprising a benzalmalonate functional group, sold under the trademark "Parsol SLX" by Hoffmann-LaRoche, 4,4-diarylbutadiene Derivatives:

1,1-dicarboxy (2,2'-diméthyl-propyl)-4,4-diphénylbutadiène and their mixtures.

The organic UV screening agents which are more particularly preferred are chosen from the following compounds:

Ethylhexyl Salicylate,

Ethylhexyl Methoxycinnamate,

Octocrylene,

Phenylbenzimidazole Sulfonic Acid,

Terephthalyidene Dicamphor Sulfonic Acid

Benzophenone-3,

Benzophenone-4,

Benzophenone-5,

4-Methylbenzylidene camphor,

Disodium Phenyl Dibenzimidazole Tetrasulfonate,

Anisotriazine,

Ethylhexyl triazone,

Diethylhexyl Butamido Triazone, 2,4,6-Tris(diisobutyl 4'-aminobenzalmalonate)-s-triazine, Methylenebis(benzotriazolyltetramethylbutyl-phenol), Drometrizole Trisiloxane, 1,1-dicarboxy (2,2'-diméthyl-propyl)-4,4-diphénylbutadiène, and their mixtures.

The cosmetic compositions according to the invention can also comprise pigments or alternatively nanopigments (mean size of the primary particles: generally between 5 nm and 100 nm, preferably between 10 nm and 50 nm) formed from coated or uncoated metal oxides, such as, for example, nanopigments formed from titanium oxide (amorphous or crystallized in the rutile and/or anatase form), iron oxide, zinc oxide, zirconium oxide or cerium oxide, which are all UV photoprotective agents well known per se. Conventional coating agents are, furthermore, alumina and/or aluminum stearate. Such coated or uncoated metal oxide nanopigments are disclosed in particular in Patent Applications EP-A-0 518 772 and EP-A-0 518 773.

The compositions according to the invention can also comprise agents for the artificial tanning and/or browning of the skin (self-tanning agents), such as, for example, dihydroxyacetone (DHA).

The compositions of the invention can additionally comprise conventional cosmetic adjuvants chosen in particular from fatty substances, organic solvents, ionic or nonionic thickeners, softeners, antioxidants, agents for combating free radicals, opacifiers, stabilizers, emollients, silicones, α-hydroxy acids, antifoaming agents, moisturizing agents, vitamins, insect repellents, fragrances, preservatives, surfactants, anti-inflammatories, substance P antagonists, fillers, polymers, propellants, basifying or acidifying agents, colorants or any other ingredient commonly used in cosmetics, in particular for the manufacture of antisun compositions in the form of emulsions.

The fatty substances can be composed of an oil or a wax or their mixtures. The term "oil" is understood to mean a compound which is liquid at ambient temperature. The term "wax" is understood to mean a compound which is solid or substantially solid at ambient temperature and for which the melting point is generally greater than 35° C. They also comprise fatty acids, fatty alcohols and esters of fatty acids which are linear or cyclic, such as derivatives of benzoic acid, trimellitic acid and hydroxybenzoic acid.

Mention may be made, as oils, of mineral oils (liquid paraffin); vegetable oils (sweet almond, macadamia, blackcurrant seed or jojoba oil); synthetic oils, such as perhydrosqualene, fatty alcohols, acids or esters (such as the $C_{12}$–$C_{15}$ alkyl benzoate sold under the trademark "Finsolv TN" by Finetex, octyl palmitate, isopropyl lanolate or triglycerides, including those of capric/caprylic acids), or oxyethylenated or oxypropylenated fatty esters and ethers; silicone oils (cyclomethicone, polydimethylsiloxanes or PDMS); fluorinated oils; or polyalkylenes.

Mention may be made, as waxy compounds, of paraffin wax, carnauba wax, beeswax or hydrogenated castor oil.

Mention may be made, among organic solvents, of lower alcohols and polyols.

Of course, a person skilled in the art will take care to choose this or these optional additional compounds and/or their amounts so that the advantageous properties, in particular the photostability, intrinsically attached to the compositions in accordance with the invention are not, or not substantially, detrimentally affected by the envisaged addition or additions.

The compositions of the invention can be prepared according to techniques well known to a person skilled in the art, in particular those intended for the preparation of emulsions of oil-in-water or water-in-oil type.

These compositions can be provided in particular in the form of a simple or complex emulsion (O/W, W/O, O/W/O or W/O/W), such as a cream, a milk, a gel or a cream gel, of a powder or of a solid tube and can optionally be packaged as an aerosol and provided in the form of a foam or spray.

When it is a question of an emulsion, the aqueous phase of the latter can comprise a nonionic vesicular dispersion prepared according to known processes (Bangham, Standish and Watkins, J. Mol. Biol., 13, 238 (1965), FR 2 315 991 and FR 2 416 008).

The cosmetic composition of the invention can be used as a composition for protecting the human epidermis or the hair against ultraviolet rays, as an antisun composition or as a make-up product.

When the cosmetic composition according to the invention is used for the protection of the human epidermis against UV rays or as an antisun composition, it can be provided in the form of a suspension or dispersion in solvents or fatty substances, in the form of a nonionic vesicular dispersion or in the form of an emulsion, preferably of oil-in-water type, such as a cream or a milk, in the form of an ointment, gel, cream gel, solid tube, powder, stick, aerosol foam or spray.

When the cosmetic composition according to the invention is used for the protection of the hair against UV rays, it can be provided in the form of a shampoo, lotion, gel, emulsion or nonionic vesicular dispersion and can constitute, for example, a rinse-out composition, to be applied before or after shampooing, before or after dyeing or bleaching, and before, during or after perming or hair straightening, a styling or treating lotion or a styling or treating gel, a lotion or a gel for blow-drying or hair setting, or a composition for perming or straightening, dyeing or bleaching the hair.

When the composition is used as a product for making up the eyelashes, eyebrows or skin, such as a treatment cream for the epidermis, foundation, lipstick tube, eyeshadow, face powder, mascara or eyeliner, it can be provided in the anhydrous or aqueous, pasty or solid form, such as oil-in-water or water-in-oil emulsions, nonionic vesicular dispersions, or suspensions.

By way of indication, for the antisun formulations in accordance with the invention which exhibit a vehicle of oil-in-water emulsion type, the aqueous phase (comprising in particular the hydrophilic screening agents) generally represents from 50 to 95% by weight, preferably from 70 to 90% by weight, with respect to the entire formulation, the oily phase (comprising in particular the lipophilic screening agents) from 5 to 50% by weight, preferably from 10 to 30% by weight, with respect to the entire formulation, and the (co)emulsifier(s) from 0.5 to 20% by weight, preferably from 2 to 10% by weight, with respect to the entire formulation.

As indicated at the beginning of the description, a subject-matter of the invention is the use of a composition as defined above in the manufacture of a cosmetic of dermatological composition intended for the protection of the skin and/or hair against ultraviolet radiation, in particular solar radiation.

Another subject-matter of the present invention is a process for improving the stability of at least one dibenzoylmethane derivative with respect to UV radiation which consists in combining, with the said dibenzoylmethane derivative, an effective amount of at least one amino-substituted 2-hydroxybenzophenone derivative as defined above.

Another subject-matter of the present invention consists of the use of an amino-substituted 2-hydroxybenzophenone derivative of formula (I) as defined above in the preparation of a cosmetic or dermatological composition comprising at least one UV screening agent of the dibenzoylmethane derivative type for the purpose of improving stability with respect to UV radiation of the said dibenzoylmethane derivative.

Concrete but in no way limiting examples illustrating the invention will now be given.

EXAMPLE 1

| | | |
|---|---|---|
| 80/20 Mixture of cetearyl alcohol and of oxyethylenated (33 EO) cetearyl alcohol (Sinnowax AO, Henkel) | | 7 g |
| Mixture of glycerol mono- and distearate (Cerasynt SD-V, ISP) | | 2 g |
| Cetyl alcohol | | 1.5 g |
| Polydimethylsiloxane (Dow Corning 200 Fluid, Dow Corning) | | 1 g |
| $C_{12}$–$C_{15}$ Alkyl benzoate (Witconol TN, Witco) | | 15 g |
| n-Hexyl 2-(4-diethylamino-2-hydroxybenzoyl)-benzoate | | 2 g |
| Butyl Methoxydibenzoylmethane (Parsol 1789, Hoffmann-LaRoche) | | 1.5 g |
| Glycerol | | 10 g |
| Preservatives | q.s. | |
| Demineralized water | q.s. for | 100 g |

EXAMPLE 2

| | | |
|---|---|---|
| Glycerol mono/distearate/polyethylene glycol (100 EO) stearate mixture (Arlacel 165 FL, ICI) | | 2 g |
| Stearyl alcohol (Lanette 18, Henkel) | | 1 g |
| Palm oil stearic acid (Stéarine TP, Stéarinerie Dubois) | | 2.5 g |
| Polydimethylsiloxane (Dow Corning 200 Fluid, Dow Corning) | | 0.5 g |
| $C_{12}/C_{15}$ Alkyl benzoate (Witconol TN, Witco) | | 15 g |
| Triethanolamine | | 0.5 g |
| n-Hexyl 2-(4-diethylamino-2-hydroxybenzoyl)-benzoate | | 1.5 g |
| Butyl Methoxydibenzoylmethane (Parsol 1789, Hoffmann-LaRoche) | | 1 g |
| Glycerol | | 5 g |
| Hexadecyl phosphate, potassium salt (Amphisol K, Hoffmann-LaRoche) | | 1 g |
| Polyacrylic acid (Synthalen K, 3V) | | 0.3 g |
| Hydroxypropyl methyl cellulose (Methocel F4M, Dow Chemical) | | 0.1 g |
| Triethanolamine | q.s. | pH 7 |
| Preservatives | q.s. | |
| Demineralized water | q.s. for | 100 g |

Each patent, patent application and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable cosmetic/dermatological sunscreen composition suited for the UV-photoprotection of human skin and/or hair, devoid of any p-methylbenzylidenecamphor, comprising (a) an effective photoprotecting amount of at least one UV-screening dibenzoylmethane compound, and (b) an effective photostabilizing amount of at least on UV-screening amino-substituted 2-hydroxybenzophenone compound having the following structural formula (I):

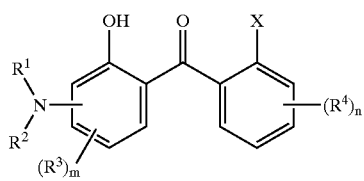

(I)

in which $R^1$ and $R^2$, which may be identical or different, are each a hydrogen atom, a $C_1$–$C_{20}$ alkyl radical, a $C_2$–$C_{10}$ alkenyl radical, a $C_3$–$C_{10}$ cycloalkyl radical or a $C_3$–$C_{10}$ cycloalkenyl radical, with the proviso that $R^1$ and $R^2$ can together form, with the nitrogen atom to which they are bonded, a 5- or 6-membered heterocyclic ring member; $R^3$ and $R^4$, which may be identical or different, are each a $C_1$–$C_{20}$ alkyl radical, a $C_2$–$C_{10}$ alkenyl radical, a $C_3$–$C_{10}$ cycloalkyl radical, a $C_3$–$C_{10}$ cycloalkenyl radical, a $C_1$–$C_{12}$ alkoxy radical, a $(C_1$–$C_{20})$alkoxycarbonyl radical, a $C_1$–$C_{12}$ alkylamino radical, a di$(C_1$–$C_{12})$alkylamino radical, an aryl radical or a heteroaryl radical which is optionally substituted, or a water-solubilizing substituent selected from among a carboxylate group, a sulfonate group or an ammonium residue; X' is a hydrogen atom or a —COOR$^5$ or —CONR$^6$R$^7$ radical; $R^5$, $R^6$ and $R^7$, which may be identical or different, are each a hydrogen atom, a $C_1$–$C_{20}$ alkyl radical, a $C_2$–$C_{10}$ alkenyl radical, a $C_3$–$C_{10}$ cycloalkyl radical, a $C_3$–$C_{10}$ cycloalkenyl radical, a —(Y'O)$_o$—Z' radical or an aryl radical; Y' is —(CH$_2$)$_2$—, —(CH$_2$)$_3$—, —(CH$_2$)$_4$— or —CH(CH$_3$)—CH$_2$—; Z' is —CH$_2$—CH$_3$, —CH$_2$CH$_2$CH$_3$, —CH$_2$—CH$_2$—CH$_2$—CH$_3$ or —CH(CH$_3$)—CH$_3$; m' is an integer ranging from 0 to 3; n' is an integer ranging from 0 to 3; and o is an integer ranging from 1 to 2, formulated into (c) a topically applicable, cosmetically/dermatologically acceptable vehicle, diluent or carrier therefor.

2. The cosmetic/dermatological sunscreen composition as defined by claim 1, wherein the ratio by weight of the at least one amino-substituted 2-hydroxybenzophenone compound of formula (I) to the at least one dibenzoylmethane compound is greater than 1.

3. The cosmetic/dermatological sunscreen composition as defined by claim 1, said at least one compound of formula (I) comprising those of the following formula (Ia):

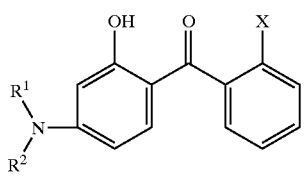

(Ia)

in which $R^1$ and $R^2$, which may be identical or different, are each a hydrogen atom, or a $C_1$–$C_{12}$ alkyl radical or together form, with the nitrogen atom to which they are bonded, a 5- or 6-membered heterocyclic ring member; X is COOR$^5$ or CONR$^6$R$^7$;

$R^5$ is a hydrogen atom, a $C_1$–$C_{12}$ alkyl radical or a $C_3$–$C_6$ cycloalkyl radical; $R^6$ and $R^7$, which may be identical or different, denote a hydrogen atom, a $C_1$–$C^{12}$ alkyl radical or a $C_5$–$C_6$ cycloalkyl radical.

4. The cosmetic/dermatological sunscreen composition as defined by claim 3, wherein formula (Ia), $R^1$ and $R^2$, which may be identical or different, are each a $C_1$–$C_4$ alkyl radical; $R^5$ is a $C_3$–$C_8$ alkyl radical; and $R^6$ and $R^7$, which may be identical or different, denote a $C_1$–$C_8$ alkyl radical.

5. The cosmetic/dermatological sunscreen composition as defined by claim 1, said at least one compound of formula (I) comprising those of the following formula (Ib):

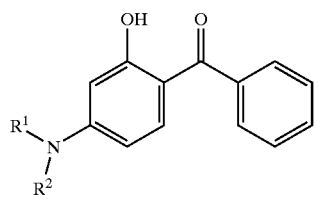

(Ib)

in which $R^1$ and $R^2$, which may be identical or different, are each a $C_1$–$C_{12}$ alkyl radical, or together form, with the nitrogen atom to which they are bonded, a 5- or 6-membered heterocyclic ring member.

6. The cosmetic/dermatological sunscreen composition as defined by claim 5, said at least one compound of formula (Ib) comprising 4-diethylamino-2-hydroxyphenyl phenyl ketone and/or 4-pyrrolidino-2-hydroxyphenyl phenyl ketone.

7. The cosmetic/dermatological sunscreen composition as defined by claim 1, said at least one compound of formula (I) comprising those of the following formula (Ic):

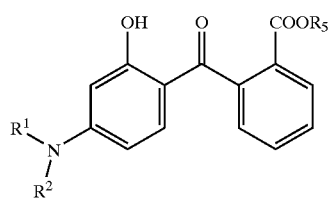

(Ic)

in which $R^1$ and $R^2$, which may be identical or different, are each denote a hydrogen atom, or a $C_1$–$C_8$ alkyl radical, or together form, with the nitrogen atom to which they are bonded, a 5- or 6-membered heterocyclic ring member; and $R^5$ is a hydrogen atom, a $C_1$–$C_{12}$ alkyl radical or a $C_3$–$C_6$ cycloalkyl radical.

8. The cosmetic/dermatological sunscreen composition as defined by claim 7, said at least one compound of formula (Ic) comprising 2-(4-pyrrolidino-2-hydroxybenzoyl)benzoic acid, methyl 2-(4-diethylamino-2-hydroxybenzoyl)benzoate, 2-ethylhexyl 2-(4-diethylamino-2-hydroxybenzoyl)-benzoate, cyclohexyl 2-(4-diethylamino-2-hydroxybenzoyl)-benzoate, n-hexyl 2-(4-diethylamino-2-hydroxybenzoyl)benzoate 2-(4-dibutylamino-2-hydroxybenzoyl)benzoic acid, methyl 2-(4-dibutylamino-2-hydroxybenzoyl)benzoate, and/or isobutyl 2-(4-dibutylamino-2-hydroxybenzoyl)benzoate.

9. The cosmetic/dermatological sunscreen composition as defined by claim 8, said at least one compound of formula (Ic) comprising n-hexyl 2-(4-diethylamino-2-hydroxybenzoyl)benzoate.

10. The cosmetic/dermatological sunscreen composition as defined by claim 1, in which the said at least one amino-substituted 2-hydroxybenzophenone compound of formula (I) comprising from 0.1 to 15 by weight, with respect to the total weight thereof.

11. The cosmetic/dermatological sunscreen composition as defined by claim 10, said at least one amino-substituted 2-hydroxybenzophenone compound of formula (I) comprising from 1 to 10% by weight, with respect to the total weight thereof.

12. The cosmetic/dermatological sunscreen composition as defined by claim 11, said at least one amino-substituted 2-hydroxybenzophenone compound of formula (I) comprising from 2 to 8% by weight, with respect to the total weight thereof.

13. The cosmetic/dermatological sunscreen composition as defined by claim 1, said at least one dibenzoylmethane compound comprising from 0.5% to 15% by weight, with respect to the total weight thereof.

14. The cosmetic/dermatological sunscreen composition as defined by claim 13, said at least one dibenzoylmethane compound comprising from 1% to 10% by weight, with respect to the total weight thereof.

15. The cosmetic/dermatological sunscreen composition as defined by claim 14, said at least one dibenzoylmethane compound comprising from 2% to 8% by weight, with respect to the total weight thereof.

16. The cosmetic/dermatological sunscreen composition as defined by claim 1, additionally comprising at least one other organic screening agent which is active in the UV-A and/or UV-B regions.

17. The cosmetic/dermatological sunscreen composition as defined by claim 16, said additional organic UV screening agent or agents being selected from among anthranilates; cinnamic derivatives; salicylic derivatives; camphor derivatives, other than p-methylbenzylidenecamphor; triazine derivatives; benzophenone derivatives, other than those of formula (I); β,β-diphenylacrylate derivatives; benzotriazole derivatives; benzalmalonate derivatives; benzimidazole derivatives; imidazolines; bisbenzoazolyl derivatives; p-aminobenzoic acid (PABA) derivatives; methylenebis (hydroxyphenylbenzotriazole) derivatives; screening polymers and screening silicones; dimers derived from α-alkylstyrene; and 4,4-diarylbutadienes.

18. The cosmetic/dermatological sunscreen composition as defined by claim 17, said organic UV screening agent or agents being selected from among Ethylhexyl Salicylate, Octocrylene, Ethylhexyl Methoxycinnamate, Phenylbenzimidazole Sulfonic Acid, Benzophenone-3, Benzophenone-4, Benzophenone-5, 4-Methylbenzylidene camphor, Disodium Phenyl Dibenzimidazole Tetrasulfonate, Anisotriazine, Ethylhexyl triazone, Diethylhexyl Butamido Triazone, 2,4,6-Tris(diisobutyl 4'-aminobenzalmalonate)-s-triazine, Drometrizole Trisiloxane, Methylenebis (benzotriazolyltetramethylbutyl-phenol), 1,1-dicarboxy(2,2'-dimethylpropyl)-4,4-dipenylbutadiene, and mixtures thereof.

19. The cosmetic/dermatological sunscreen composition as defined by claim 1, additionally comprising coated or uncoated metal oxide pigments or nanopigments.

20. The cosmetic/dermatological sunscreen composition as defined by claim 19, said pigments or nanopigments comprising coated or uncoated titanium dioxide, zinc oxide, iron oxide, zirconium oxide or cerium oxide, and mixtures thereof.

21. The cosmetic/dermatological sunscreen composition as defined by claim 1, additionally comprising at least one agent for the artificial tanning and/or browning of the skin.

22. The cosmetic/dermatological sunscreen composition as defined by claim 1, additionally comprising at least one adjuvant or additive selected from among fatty substances, organic solvents, ionic or nonionic thickeners, softeners, antioxidants, agents for combating free radicals, opacifiers, stabilizers, emollients, silicones, α-hydroxy acids, antifoaming agents, moisturizing agents, vitamins, insect repellents, fragrances, preservatives, surfactants, anti-inflammatories, substance P antagonists, fillers, polymers, propellants, basifying or acidifying agents, or colorants.

23. The cosmetic/dermatological sunscreen composition as defined by claim 1, formulated as a nonionic vesicular dispersion, an O/W or W/O emulsion, a cream, a milk, a gel, a cream gel, a suspension, a dispersion, a powder, a solid tube, a foam or a spray.

24. The cosmetic/dermatological sunscreen composition as defined by claim 1, formulated as a makeup for the eyelashes, eyebrows or skin and provided in the anhydrous or aqueous, pasty or solid form, in the form of an emulsion, of a suspension or of a dispersion.

25. The cosmetic/dermatological sunscreen composition as defined by claim 1, formulated for the protection of the hair against ultraviolet rays and provided in the form of a shampoo, of a lotion, of a gel, of an emulsion, or of a nonionic vesicular dispersion.

26. A regime or regimen for photoprotecting human skin and/or hair against the deleterious effects of ultraviolet irradiation, comprising topically applying thereon an effective amount of a cosmetic/dermatological sunscreen composition that does not contain any p-methylbenzylidenecamphor, but which comprises (a) an effective photoprotecting amount of at least one UV-screening dibenzoylmethane compound, and (b) an effective photostabilizing amount of at least one UV-screening amino-substituted 2-hydroxybenzophenone compound having the following structural formula (I):

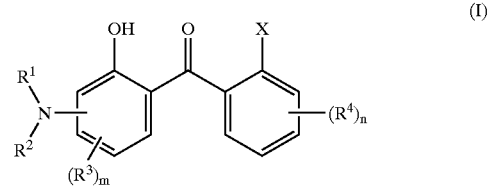

in which $R^1$ and $R^2$, which may be identical or different, are each a hydrogen atom, a $C_1$–$C_{20}$ alkyl radical, a $C_2$–$C_{10}$ alkenyl radical, a $C_3$–$C_{10}$ cycloalkyl radical or a $C_3$–$C_{10}$ cycloalkenyl radical, with the proviso that $R^1$ and $R^2$ can together form, with the nitrogen atom to which they are bonded, a 5- or 6-membered heterocyclic ring member; $R^3$ and $R^4$, which may be identical or different, are each a $C_1$–$C_{20}$ alkyl radical, a $C_2$–$C_{10}$ alkenyl radical, a $C_3$–$C_{10}$ cycloalkyl radical, a $C_3$–$C_{10}$ cycloalkenyl radical, a $C_1$–$C_{12}$ alkoxy radical, a $(C_1$–$C_{20})$alkoxycarbonyl radical, a $C_1$–$C_{12}$ alkylamino radical, a di($C_1$–$C_{12}$)alkylamino radical, an aryl radical or a heteroaryl radical which is optionally substituted, or a water-solubilizing substituent selected from among a carboxylate group, a sulfonate group or an ammonium residue; X' is a hydrogen atom or a —$COOR^5$ or —$CONR^6R^7$ radical; $R^5$, $R^6$ and $R^7$, which may be identical or different, are each a hydrogen atom, a $C_1$–$C_{20}$ alkyl radical, a $C_2$–$C_{10}$ alkenyl radical, a $C_3$–$C_{10}$ cycloalkyl radical, a $C_3$–C cycloalkenyl radical, a —$(Y'O)_o$—Z' radical or an aryl radical; Y' is —$(CH_2)_2$—, —$(CH_2)_3$—, —$(CH_2)_4$— or —CH—$(CH_3)$—$CH_2$—; Z' is —$CH_2$—$CH_3$, —$CH_2CH_2CH_3$, —$CH_2$—$CH_2$—$CH_2$—$CH_3$ or —$CH(CH_3)$—$CH_3$; m' is an integer ranging from 0 to 3; n' is an integer ranging from 0 to 3; and o is an integer ranging from 1 to 2, formulated into (c) a topically applicable, cosmetically/dermatologically acceptable vehicle, diluent or carrier therefor.

27. A method for photostabilizing at least one UV-screening dibenzoylmethane compound in the absence of any p-methylbenzylidenecamphor, comprising formulating therewith an effective stabilizing amount of at least one amino-substituted 2-hydroxybenzophenone compound as defined in claim 1.

* * * * *